(12) United States Patent
Abbate et al.

(10) Patent No.: US 6,198,097 B1
(45) Date of Patent: Mar. 6, 2001

(54) PHOTOCHARGE MICROSCOPE

(75) Inventors: Agostino Abbate, Clifton Park; Julius Frankel, Rensselaer; Pankaj K. Das, Latham, all of NY (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/061,843

(22) Filed: Apr. 15, 1998

(51) Int. Cl.[7] .................................................. G01N 23/227
(52) U.S. Cl. ............................................................. 250/306
(58) Field of Search ............................................... 250/306

(56) References Cited

U.S. PATENT DOCUMENTS 5,105,305 * 4/1992 Betzig et al. ..................... 250/458.1
5,393,980 * 2/1995 Yost et al. ........................... 250/306
5,464,977 * 11/1995 Nakagiri et al. ..................... 250/306

* cited by examiner

*Primary Examiner*—Jack I. Berman
(74) *Attorney, Agent, or Firm*—John F. Moran; Michael C. Sachs

(57) ABSTRACT

An apparatus and/or system is described which uses the photocharge voltage concept in lieu of optical scattering techniques to measure surface topology and properties of materials. The system is based on the measurement of a small electrical potential difference which appears on any solid body when subjected to illumination by a modulated laser light. This voltage is proportional to the induced change in the surface electrical charge and is capacitively measured on various materials. The characterization of coatings to be used inside the base of guns is just one possible application for use by the U. S. Army.

16 Claims, 5 Drawing Sheets

| MATERIAL | PHOTOCHARGE VOLTAGE [μV] |
|---|---|
| STEEL | 12 |
| ALUMINUM | 5.5 |
| FERRITE (Fe-Mg-Mn-In) | 36 |
| BLACK RUBBER (TIRE) | 22 |
| WHITE COTTON FABRIC | 180 |
| NEWSPAPER | 200 |
| PEGMATITE STONE | 215 |
| STYROFOAM | 140 |
| WOOD | 20 |
| SILICON (SEMICONDUCTOR) | 40,000 |
| COPPER (POLISHED SURFACE) | 29 |
| COPPER (ROUGH SURFACE) | 10 |

PHOTOCHARGE MICROSCOPE

U.S. GOVERNMENT INTEREST

The invention described herein may be manufactured, used and licensed by or for the Government for Government purposes without payment to me of any royalties therein.

BACKGROUND OF THE INVENTION

I. Field of Invention

This invention applies to the field of systems and/or various apparatus which are used to inspect and measure surface topology and properties of materials. Such systems are used to measure the variations in surface roughness and to detect the presence of cracks and surface flaws with high spatial resolution. The field also encompasses optical characterization methods and apparatus.

II. Background of the Invention

Conventional scanning surface inspection systems currently use optical scattering techniques which are limited in their application because they use light scattering to measure surface topology. The system being proposed herein is based on the measurement of a small electrical potential difference which appears on any solid body when subjected to illumination by a modulated laser light. This voltage is proportional to the induced change in the surface electrical charge and is capacitively measured on various materials such as conductors, semiconductors, ceramics, dielectrics and biological objects. Experiments are easily repeated, and the amplitude of the detected signal depends on the type of material under investigation, and on the surface properties of the sample.

The design of a measuring system capable of performing photocharge voltage measurements for microscopic characterization of material surfaces is here described. Since the measured quantity, the photocharge voltage (PV) is observed on any kind of material present at the surface of the sample under investigation, e.g. semiconductor, insulator and metal, PV measurements can be easily used to evaluate any morphological variation or discontinuity at the surface, as well as in any spatial variation of the surface charge in a uniform semiconductor area.

The spatial variation of PV can be used to evaluate the surface conditions of the sample even with metalization and the variation of the PV due to the monochromatic bias light are used to characterize the surface states.

The proposed technique is completely contactless and it can be used in a high resolution microscope system. In fact, applications are numerous, from thin film and surface mechanical characterization to in-line nondestructive characterization of semiconductor wafers during the various stages of integrated circuits fabrication.

SUMMARY OF INVENTION

The measurement system proposed herein uses a modified Kelvin probe concept so that spatial variations of the photocharge voltage (PV) can be measured. A modulated laser output is used to optically excite the sample. The output electrical signal from the shielded sample is obtained from the difference in electrical potential. Appropriate instrumentation complete the entire system to precisely, accurately monitor the photocharge voltage.

It is an object of this invention to provide a system for the optical characterization of the surface topology and properties of materials.

It is another object of this invention to provide that the technique remain contactless and be fitted in an high resolution microscope system which can measure the spatial variation of the photocharge voltage (PV) to evaluate the surface conditions of a sample even with metalization. The variation of the PV due to monochromatic bias light is used to characterize the surface states.

It is yet another object of this invention to provide a system with the minimum precautions and constraints in its use.

DETAILED DESCRIPTION OF THE PREFERRED EMBODIMENT

Figure 1:
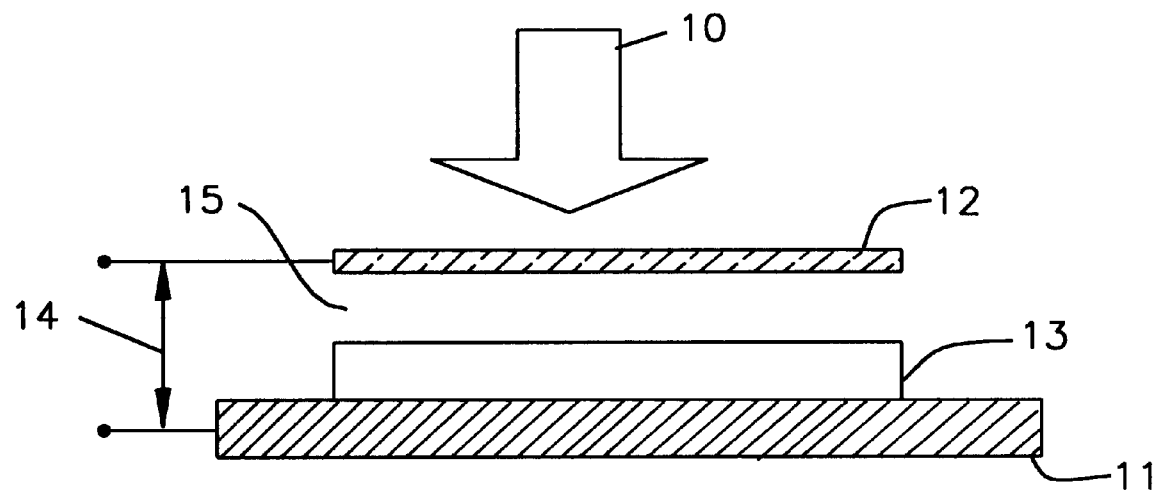
FIG. 1 is a conceptual diagram of a semiconductor sample under laser illumination depicting the location of the voltage potential.

Using FIG. 1, the operating principle of the system is based on the small electrical potential 14 difference which appears on any solid body 13 when subjected to illumination by a modulated light beam generated by laser 10. This voltage was measured on various materials such as conductors, semiconductors, ferrites, ceramics, dielectrics and biological objects. The amplitude of the detected signal such as that graphed at FIG. 2 depends on the type of material under investigation, and on the surface properties of the sample. Typical values measured for different samples are given in Table 1 at FIG. 8. The large variety of samples clearly shows the universality of this effect.

The mechanism of generation of the photocharge voltage 14 is different for the various types of materials, but nevertheless it has to be emphasized that a potential change 14 can be measured in any solid as a response to illumination. In metals, the electron relaxation time is of the order of 10–15 sec.; therefore any photogeneration of free electrons cannot alone be responsible for the photo-charge effect. A possible explanation of the effect can be made by considering the attenuation of an electromagnetic wave incident on a conductive surface. The so-called skin effect causes the redistribution of carriers, resulting in an electrostatic field.

At the surface of a conductor there is the so-called double layer, which is usually smaller than the skin depth of the electromagnetic (e.m.) laser irradiation. The incident electromagnetic waves thus penetrates completely through the double layer, in which a non-uniform distribution of charges is present. A force is thus generated inside this layer, which results in a localized change of the magnitude of the double-layer potential. It has been pointed out that it is very unlikely that the measured signals are due to the thermal e.m.f., induced by heating of the metal contacts, since a large number of materials studied are good heat insulators.

The photocharge voltage 14 in dielectric materials can be explained with the assumption that dipole molecules are absorbed on the surface of the solid bodies. The incident light induces a force acting on these molecules, proportional to the gradient of the electrical permittivity of the medium, as in the case of conductors. This results in a redistribution of the total charge with the appearance of a small potential difference.

The photoconductivity and the photovoltaic effect are believed to be the largest contributors to the photo-charge effect for the case of semiconductor samples. Optical surface photovoltage has been used in the past to characterize semiconductors. However, the photocharge voltage 14 is measured for light of all photon energies and is caused by the redistribution of charges already present near the surface. Since this voltage is measured capacitively, no net current is present across the sample, thus the photo-induced charge is constrained within the space charge region of the semiconductor sample, resulting in a redistribution of the total charge compensated by a change in the potential inside the semiconductor space charge region. In the steady state, the optical generation of free charge carriers is thus balanced by the recombination at the surface and by diffusion in the bulk.

The response of the semiconductor sample to laser 10 illumination is thus influenced by the equilibrium conditions existing in the material prior to the laser pulse. The amplitude of the detected voltage $V_L$ is a function of: (a) the surface space region, through the surface potential $\phi_s$, the width of the space charge region and its capacitance $C_{sc}$; (b) the surface states, through the surface recombination velocity $S_p$ which is a function of the density of surface states; (c) the bulk trap levels, through the lifetime $\tau_p$ and average depth $L_p$. In photocharge voltage spectroscopy measurements, the sample 13 is illuminated by both a steady state monochromatic light, and a pulsed laser 10. When the sample is illuminated by a constant monochromatic light of energy $E_M = h \mu M$ and with an intensity $\Phi_M < \Phi_L$, the conditions of the sample, prior to the laser 10 pulse, are varied. In this case the optical generation is represented by two terms: the first, represented by the term $q\Phi L/\alpha L$ which represents the number of free carriers generated per unit time and area by the laser pulse, where q is the electron's electric charge and the product $\alpha L$ represents the effective area of the optical interaction. The second term is represented by the product $q\Phi M\sigma^o N_t$, where $\sigma^o$ and $N_t$ represent the optical cross section and the density of the trap level involved in the photo-generation process, respectively. A simplified expression for the photocharge voltage in semiconductors is thus given as:

$$V_L = \frac{q}{C_{SC}} \cdot \frac{\frac{\phi_L}{\alpha L} \pm \sigma^o N_t \phi_M}{\left(S_p + \frac{L_p}{\tau_p}e^{-q\phi_s/KT}\right)} \quad (1)$$

As can be seen from equation 1, the measured voltage 14 is dependent on the surface potential $\phi_s$ through the exponential factor connected with the recombination current in the bulk, but also through the semiconductor capacitance $C_{sc}$. It is evident that the higher the value of $\phi_s$ the larger is the amplitude of the PV. This is expected, since the presence of a surface band bending is responsible for the separation of the photogenerated electrons and holes, and for the barrier which impedes diffusion of minority carriers in the bulk.

Figure 3:
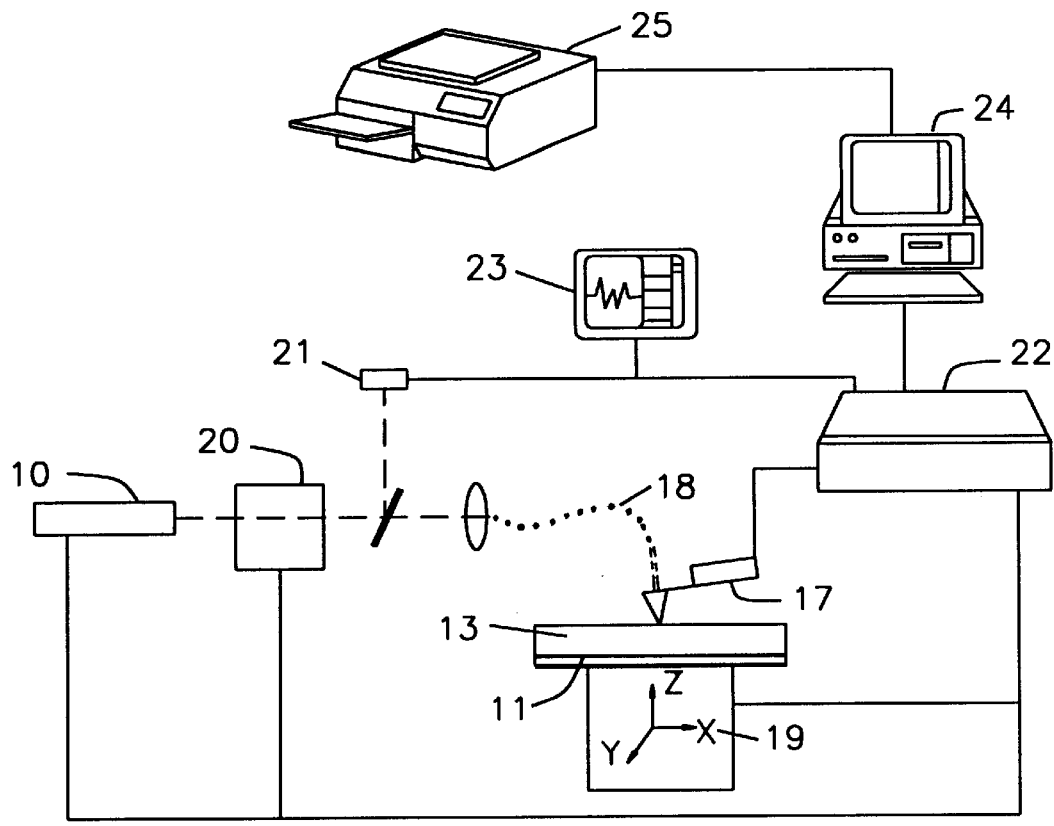
FIG. 3 is the block diagram of the photocharge microscope system used in photocharge measurements.

Turning now to FIG. 3 which is a block diagram of a typical experimental setup used in photocharge measurements. This system utilizes a modified Kelvin probe concept, in which the specimen 13 is placed on a metallic plate 11 that is mounted on an electrically insulating platform with a high resolution X-Y positioning stage 19 so that spatial variations of the PV can be measured. The He—Ne laser 10, used to optically excite the sample 13, is modulated as a sequence of bursts, using either a mechanical chopper 20 or an acousto-optic modulator 20, with variable pulse length and period. A typical repetition rate for the chopper 20 is 15 Hz with light pulses of approximately 5 ms in duration and the amplitude of the detected signal is of the order of mVolts, as shown at FIG. 3. The light is incident on the sample 13, placed in a metal box to shield it from external electrical disturbance. The output electrical signal is obtained from the difference in electrical potential between the back metal plate 11 which is pressed against the back surface of the sample 13 and the front contact, made by a transparent metal plate 12 with a dielectric spacer 15 as shown at FIG. 1.

Figure 2:
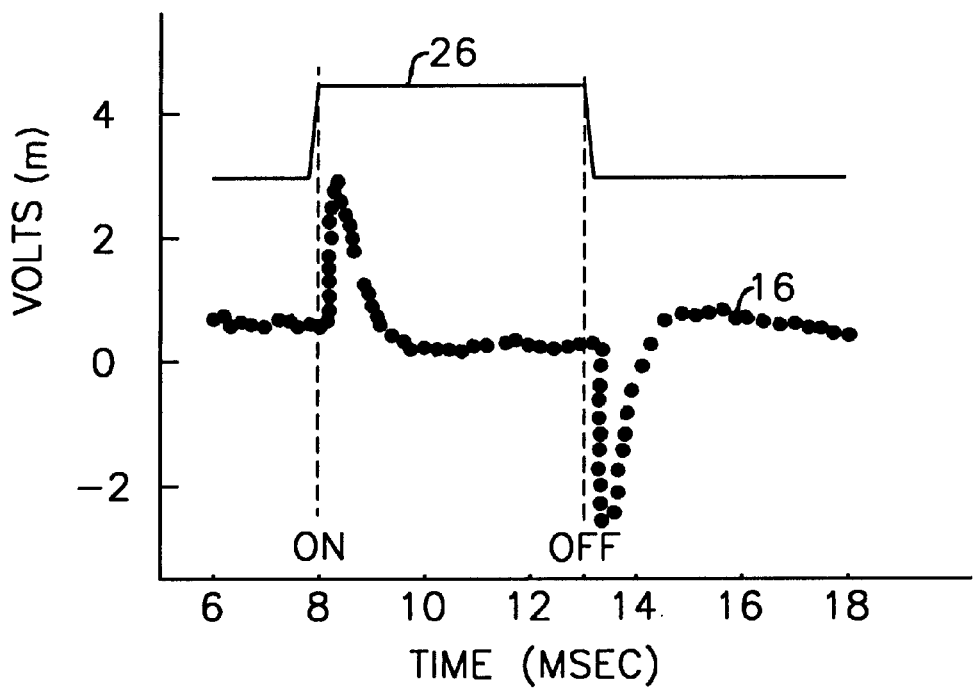
FIG. 2 is the two-dimensional graph of a reference signal and PV scan output of a ample (Zn-doped GaAs semiconductor) optically excited by an He—Ne laser and modulated by a mechanical chopper.

The instrumentation to monitor the photocharge voltage 14 is relatively simple. The output of the sample is connected to a very high input impedance amplifier with adjustable band pass filter 22. The output of the amplifier is connected to a digital oscilloscope 23 (for example the Hewlett Packard 54100D) and to a lock-in amplifier (for example the EG&G Princeton Applied Research 186A). The contacts to the sample are connected to the input resistance of the amplifier, so that a variation in the incident photon intensity, as the one induced by the chopper 20, results in a current transient. The lock-in output thus corresponds to the integral over time of this transient, and thus the total charge induced by the laser 10 illumination. The synchronization to the oscilloscope 23 and the lock-in amplifier 22 is supplied by the chopper 20. A typical reference signal 26 to the lock-in amplifier 22 is shown in FIG. 2, and the correspondent PV for a Zn-doped GaAs semiconductor sample 16 with a resistivity of 0.1 Ω-cm, is given.

A monochromator is also used to vary the surface electrical conditions prior to the laser pulse. The wavelength and intensity of the monochromatic light can be varied and the relative amplitude of the PV is measured and stored in the PC computer 24. In the presented measurements the He—Ne laser 10 has a measured output power of 8 mWatt, with a calculated photon flux $\Phi_L$ of $3\times10^{18}$ $cm^{-2}$ $sec^{-1}$. A High-Intensity Baush & Lomb monochromator, with a calculated photon flux $\Phi_M$ is $1.6\times10^{17}$ $cm^{-2}$ $sec^{-1}$, was also used in the presented experiments.

By integrating the PV measurements with optical fiber technology it will be possible to obtain higher spatial resolution. Current advances in probe 18 and feedback techniques have brought near-field scanning microscopy to the point where the resolution of the probe 18 is of the order of 12 nm. In 1991, Eric Betzig and Jay Trautmann of AT&T Bell Laboratories (Murray Hill, N.J.) invented and patented a hybrid near-field/fiber-laser probe, with a high photon flux. This has been proposed for optical data storage applications. An increase of the photon flux by a factor of $10^3$–$10^4$ over earlier passive near-field probe-tip designs was reported. A photon flux of $10^{15}$ photons/sec with a spatial resolution of 10 nm is thus obtainable for the proposed measurement system. The increased photon flux with accurate spatial resolution has been achieved using a fiber probe 18 connected to the output of the laser 10 cavity, acting as one end reflector. The other end of the fiber is tapered with a final aperture of approximately 10 nm. A $Nd^{3+}$-doped fiber was used, and investigations have been directed into using $Yb^{3+}$ fibers, which have the largest absorption coincident with commercially available 980 nm laser diodes. The bandwidth of the proposed probe 18 is of the order of MHz, well beyond our needs.

Using FIG. 3 we now summarize the operation of the proposed photocharge microscope. The sample 13 is placed on top of a ground plate 11 and the probe 18 is positioned on top of the opposite surface 13. The position of the probe 18 in the direction normal to the surface of the sample 13 is accurately controlled (approximately 10 nm) using a tip/cantilever assembly 17. With today's sophisticated semiconductor technology, the probe 18 tip can be mass produced with consistently shaped, very sharp tips of different shapes (for probing different morphologies and scales of surface features) and materials (conducting, magnetized, etc.). The optical fiber with a tapered end and a final aperture of 10 nm, will be incorporated in the probe 18 tip assembly, to assure the maximum closeness of the fiber end to the sample and reduce diffraction of the laser 10 beam. The probe 18 is incorporated into a feedback system so that its distance to the surface of the sample 13 is kept constant. A computer-controlled two-dimensional scanning system will be used to move the probe 18 and/or the sample for rapid automated scanning.

The photocharge effect involves the appearance of an electric potential 14 between a sample 13, irradiated with a intensity-modulated light 10, and a contact with zero potential. Coupling between the two bodies is only capacitive, and the magnitude of the measured signal depends on the state of the surface being irradiated and on the distance of the pick-up probe to the sample. Therefore, in order to develop a reliable technique for surface characterization, the coupling must be kept constant during scanning of the sample 13. We propose to include in the probe system the probe 18 and feedback techniques which have been developed for near-field scanning microscopy and Atomic Force Microscope. Using the similar techniques the distance between the probe 18 pick-up electrode and the sample 13 can be maintained constant within the necessary limit of detection. This approach will assure that any variation in the detected voltage can be related to changes in the photocharge voltage.

By integrating the fiber-laser probe 18 into a commercially available Atomic Force Microscope probe, as the commercially available Nanoscope Dimension 3000 by Digital Instruments, it is possible to perform photocharge voltage measurements on semiconductor samples with a spatial resolution of 10 nm. The NanoScope Dimension 3000 is capable to measure samples up to 8 inches in diameters. The system currently supports atomic force and scanning tunneling microscopy.

The photocharge microscope can be used to scan PV indicative of surface properties of different types of solid materials. By scanning information locally, varying properties of the material may be obtained. Thus, an image of the topology of a surface or of the variations of its photo-response to the laser pulse can be plotted.

A possible application of this system for the U.S.Army lies in the characterization of coatings to be used in the inside bore of gun barrels. The photocharge microscope can be used to map with very high spatial resolution the surface morphology of coatings deposited on gun steel, as well as cracks and flaws. Furthermore, since the photocharge voltage seems to be due to a force acting on the optically induced surface charge, it must be sensitive to the presence of other elastic or plastic deformation already present in the material, for example, surface stresses. Any material property which affects the optical and mechanical properties at the surface can be spatially mapped using the photocharge microscope.

Figure 4:
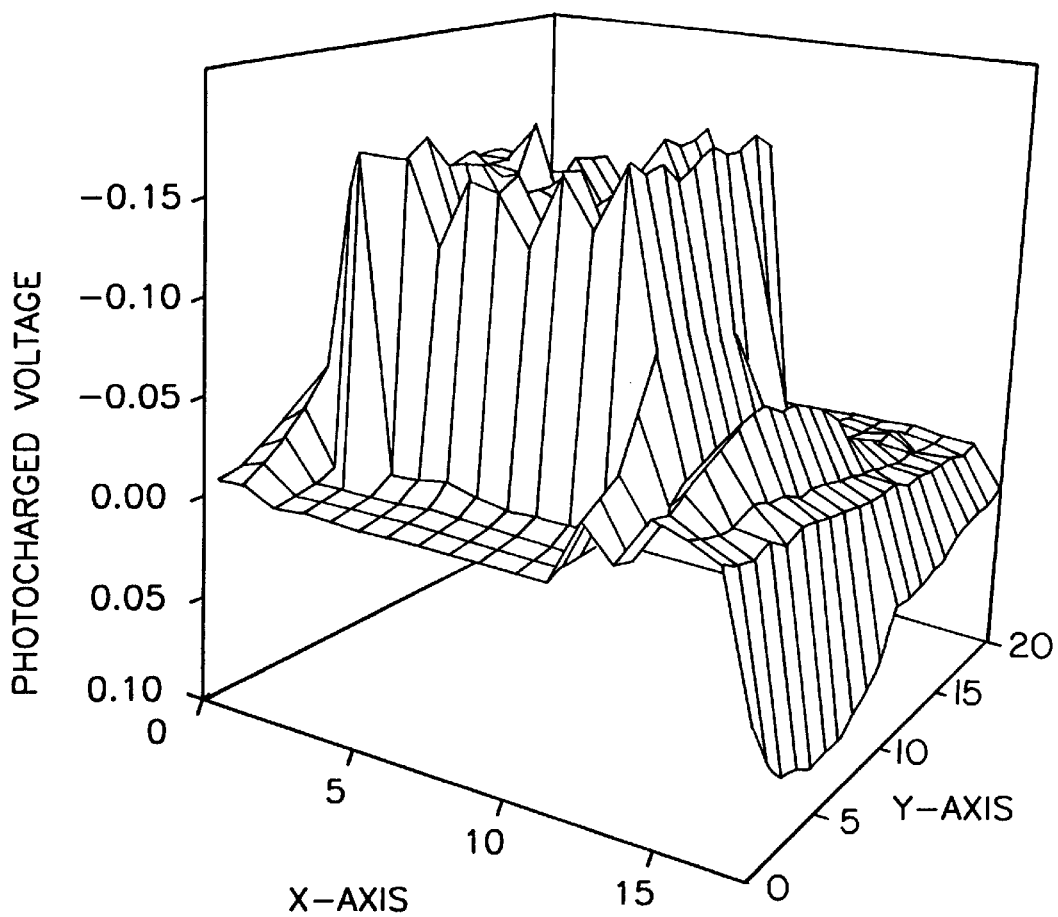
FIG. 4 is the three-dimensional plot of a PV scan of an amorphous silicon solar cell.
Figure 5:
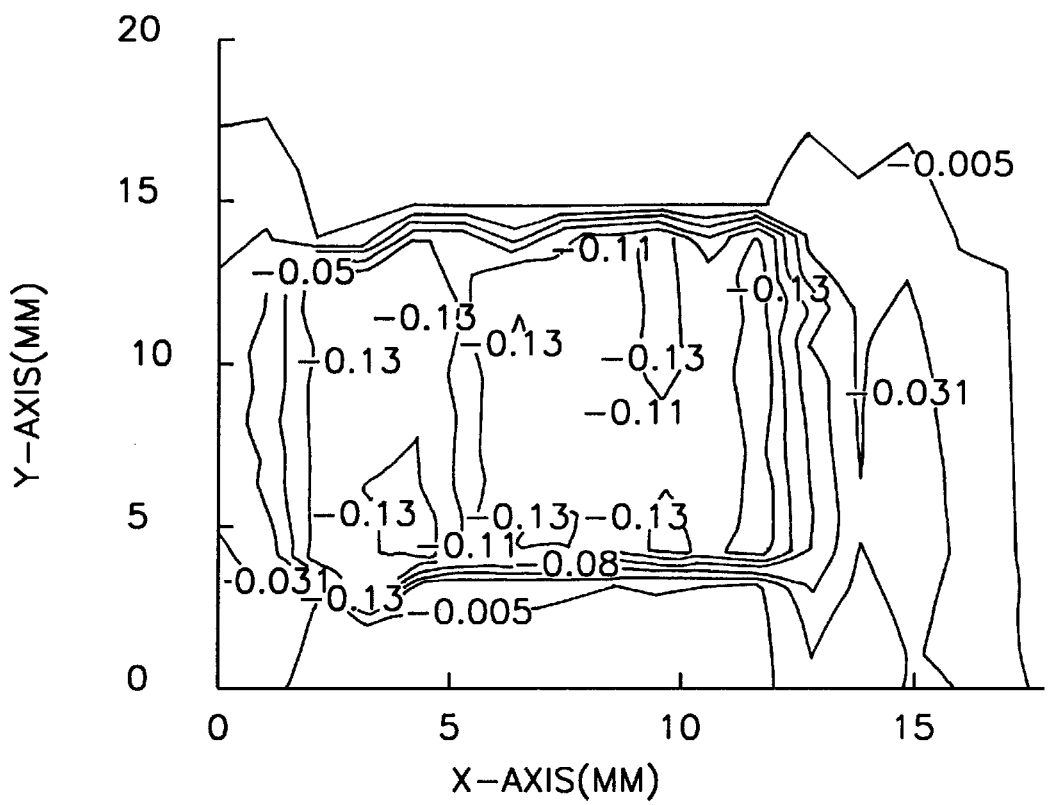
FIG. 5 is the contour plot of the PV scan of the amorphous silicon solar cell previously described by its three-dimensional plot.

A representative example of the application of the photocharge microscope is given in FIG. 4 which represents the three-dimensional PV scan of an amorphous silicon solar cell. The solar cell is composed by a layered semiconductor film of about 1000 Å in thickness, sandwiched between two conductors. The bottom contact is a transparent metal, while the top is a square contact made of aluminum. The x- and y-axis of the plot represent the dimensions of the sample area scanned in this test. In this case a 20×20 mm area was probed using the prototype system. The z-axis represents the amplitude of the PV measured at the point of coordinate (x, y). The sample area covered by the top metal contact is clearly distinguishable as the PV amplitude is higher in value. A small strip of the sample is only covered by the bottom transparent contact which shows a PV of inverted polarity. The contour plot of the same measurement is shown at FIG. 5. One line of this scan is plotted in FIG. 6A.

Figure 6A:
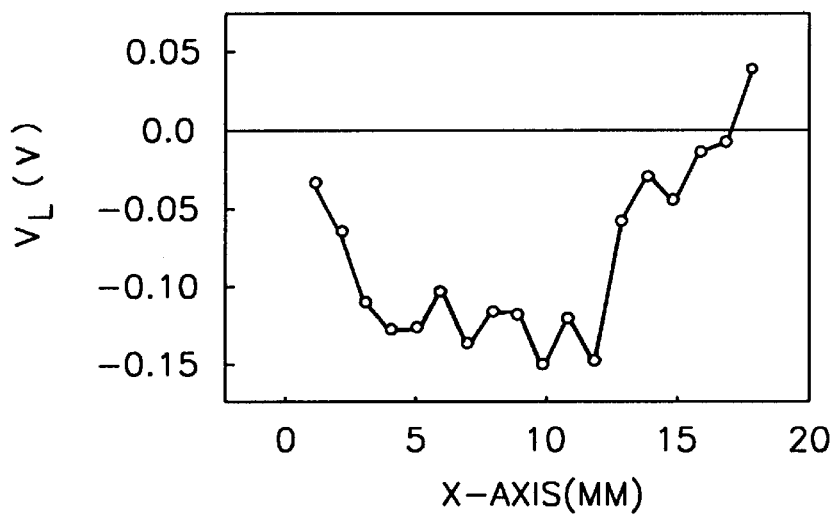
FIG. 6A is the one line scan of the thin amorphous silicon film showing the difference in photocharge voltage due to different surface conditions as related to the composition of the sample at FIG. 6B.
Figure 6B:
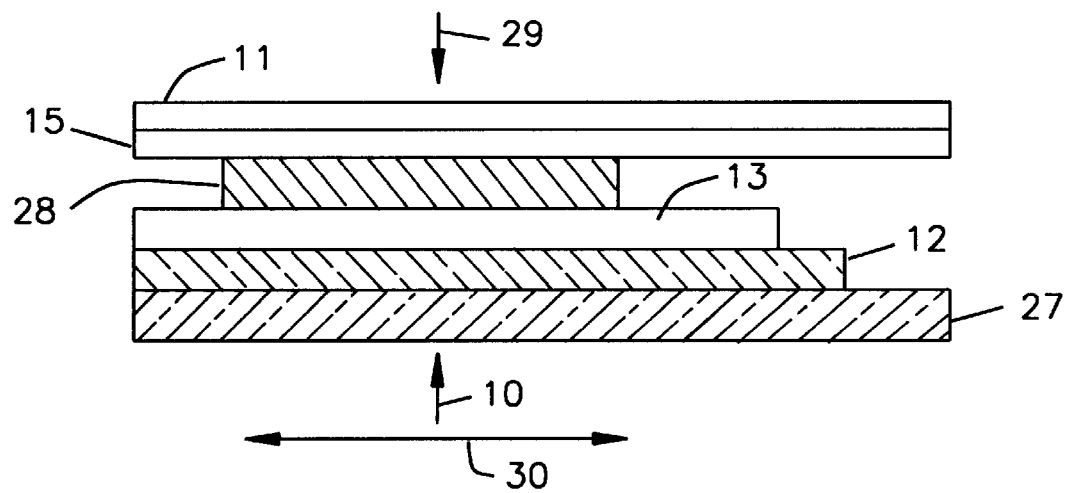
FIG. 6B is the experimental set up of a thin amorphous silicon film grown on a glass substrate which was scanned with a photocharge voltage microscope.

In FIG. 6B, the geometrical description of the cell is given, while the measured PV voltage is represented in the bottom part of the figure so that the measurement, shown in FIG. 6A can be easily related to the composition of the sample. Three different regions are clearly distinguishable by the spatial variation in PV amplitude. These regions are: only bottom transparent metal, bottom metal and p-i-n layers, and finally the complete solar cell. In this experiment a prototype of the photocharge microscope was then used to image the topological and material properties changes at the surface of the solar cell, which could be verified by optical means.

Figures 7, 8:
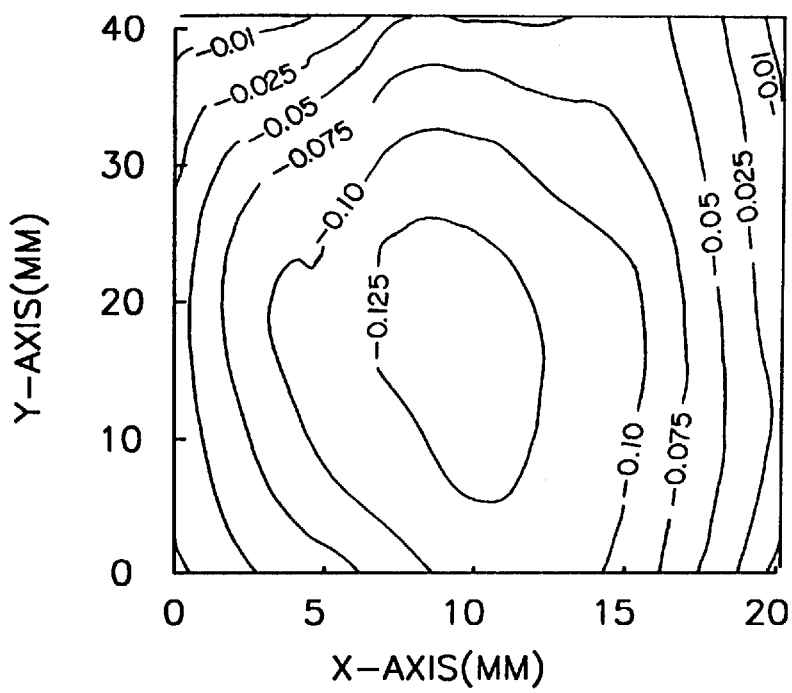
FIG. 7 is a contour plot of the stress distribution existing at the substrate/thin film interface of a thin amorphous silicon film grown on a glass substrate.
FIG. 8. is a table of the typical values of the photocharge voltage measured for different samples.

Using the same experimental setup, the stress distribution existing at the substrate/thin interface of a thin amorphous silicon film grown in a glass substrate was imaged. FIG. 7 depicts the photo voltage (PV) measurements. The difference in PV obtained in the image is due to the different conditions of the surface due to the stress and it could not be obtained using an optic microscope or any other scanning type microscope such as the Atomic Force microscope. The spatial variation in PV is to be attributed to the non-uniformity in the photo-generation and distribution of charges in the film due to stress.

Thus, it is apparent that in accordance with the present invention, a functional design that fully satisfies the objectives aims and advantages is set forth above. The experiments described above suggest the utilization of the photocharge microscope for the characterization of thin films and coatings both in the semiconductor industry and in other fields in which thin films are used. While the invention has been described in conjunction with a specific embodiment, it is evident that many alternatives, modifications and variations will become evident to those skilled in the art in light of the foregoing description. Accordingly, it is intended that the present invention embrace all such alterations, modifications, and variations as fall within the spirit and broad scope of the appended claims.

What is claimed is:

1. An apparatus which employs the photocharge voltage concept in lieu of optical scattering techniques to detect and image variations in material composition and properties at the surface and subsurface as well as surface contaminants and material defects, comprising:

means to place and maintain the said material composition;

means to excite the said material composition;

means to measure the spatial variations of the said photocharge voltage;

means to monitor the said photocharge voltage; and means for varying the surface electrical conditions of the said material composition.

2. The apparatus as defined by claim 1 wherein the means to place and maintain the material composition comprises a metal plate mounted on an electrically insulating platform.

3. The apparatus as defined by claim 1 wherein the means to excite the said material composition is a laser.

4. The apparatus as defined by claim 1 wherein the means to measure the spatial variations of the said photocharge voltage comprises a high resolution x-y positioning stage onto which the said means to place and maintain the material composition rests; and a hybrid near-field doped optical fiber incorporated into the output of a laser cavity to form an integrated probe with a high photon flux accurately controlled using a tip/cantilever assembly.

5. The apparatus as defined by claim 1 wherein the means to monitor the said photocharge voltage comprises a digital oscilloscope which receives the output from a high input impedance amplifier with adjustable bandpass filter generated by the said material composition upon excitation; and a PC computer allowing for the automated scanning to be controlled.

6. The apparatus as defined by claim 1 wherein the means to vary the surface electrical conditions of the said composition comprises a monochromator.

7. The apparatus as defined by claim 1 wherein the said photocharge voltage generated is defined by the relationship:

$$V_L = \frac{q}{C_{SC}} \cdot \frac{\frac{\phi_L}{\alpha L} + \sigma^o N_t \phi_M}{S_p + \frac{L_p}{\tau_p} e^{-q\phi_s/KT}} \quad (1)$$

wherein $V_L$ is the detected voltage; $\phi_s$ is the surface band binding; $C_{sc}$ is the capacitance of the space charge region; $S_p$ is the surface recombination velocity; $\tau_p$ is the lifetime of the bulk trap levels; $L_p$ is the average depth of the bulk trap levels; $q\phi_L/\alpha_L$ is the number of free carriers generated per unit time and area by the said means which excite the material where q is the electron's electric charge; $\alpha_L$ is the effective area of the optical interaction; $\sigma^o$ is the optical cross section; and $N_t$ is the density of the trap level involved in the said photocharge voltage.

8. The apparatus as defined by claim 3 wherein the laser is a He—Ne laser with a measured output of 8 m watt and photon flux $Q_L$ of $3 \times 10^{18}$ cm$^{-2}$ sec$^{-1}$ modulated as a sequence of bursts wherein said bursts are caused by a mechanical chopper or an acoustic-optic modulator with variable pulse length and period.

9. A system which employs the photocharge voltage concept in lieu of optical scattering techniques to detect and image variations in material composition and properties at the surface and subsurface as well as surface contaminants and material defects, comprising:

means to place and maintain the said material composition;

means to excite the said material composition;

means to measure the spatial variations of the said photocharge voltage;

means to monitor the said photocharge voltage; and means for varying the surface electrical conditions of the said material composition.

10. The system as defined by claim 9 wherein the means to place and maintain the material composition comprises a metal plate mounted on an electrically insulating platform.

11. The system as defined by claim 9 wherein the means to excite the said material composition is a laser.

12. The system as defined by claim 9 wherein the means to measure the spatial variations of the said photocharge voltage comprises a high resolution x-y positioning stage onto which the said means to place and maintain the material composition rests; and a hybrid near-field doped optical fiber incorporated into the output of a laser cavity to form an integrated probe with a high photon flux accurately controlled using a tip/cantilever assembly.

13. The system as defined by claim 9 wherein the means to monitor the said photocharge voltage comprises a digital oscilloscope which receives the output from a high input impedance amplifier with adjustable bandpass filter generated by the said material composition upon excitation; and a PC computer allowing for the automated scanning to be controlled.

14. The system as defined by claim 9 wherein the means to vary the surface electrical conditions of the said composition comprises a monochromator.

15. The system as defined by claim 9 wherein the said photocharge voltage generated is defined by the relationship:

$$V_L = \frac{q}{C_{SC}} \cdot \frac{\frac{\phi_L}{\alpha L} \pm \sigma^o N_t \phi_M}{\left(S_p + \frac{L_p}{\tau_p} e^{-q\phi_s/KT}\right)} \quad (1)$$

wherein $V_L$ is the detected voltage; $\phi_s$ is the surface band binding; $C_{sc}$ is the capacitance of the space charge region; $S_p$ is the surface recombination velocity; $\tau_p$ is the lifetime of the bulk trap levels; $L_p$ is the average depth of the bulk trap levels; $q\phi_L/\alpha_L$ is the number of free carriers generated per unit time and area by the said means which excite the material where q is the electron's electric charge; $\alpha_L$ is the effective area of the optical interaction; $\sigma^o$ is the optical cross section; and $N_t$ is the density of the trap level involved in the said photocharge voltage.

16. The system as defined by claim 11 wherein the laser is a He—Ne laser with a measured output of 8 m watt and photon flux $Q_L$ of $3 \times 10^{18}$ cm$^{-2}$ sec$^{-1}$ modulated as a sequence of bursts wherein said bursts are caused by a mechanical chopper or an acoustic-optic modulator with variable pulse length and period.

* * * * *